United States Patent [19]

Duelfer et al.

[11] Patent Number: 4,996,212

[45] Date of Patent: Feb. 26, 1991

[54] ANTIINFLAMMATORY AND ANTI-HYPERPROLIFERATIVE COMPOUNDS

[75] Inventors: Timothy Duelfer, Morris Plains; David J. Blythin, North Caldwell, both, N.J.

[73] Assignee: Schering Corporation, Kenilworth, N.J.

[21] Appl. No.: 454,658

[22] Filed: Dec. 21, 1989

[51] Int. Cl.$^5$ ................ C07D 471/14; A61K 31/435
[52] U.S. Cl. .................... 514/293; 514/293; 544/182; 544/295; 544/296; 544/238; 544/333; 544/357; 544/405; 546/82
[58] Field of Search ............ 546/82; 544/295, 296, 544/333, 357, 405, 182, 238; 514/293

[56] References Cited

U.S. PATENT DOCUMENTS

| | | | |
|---|---|---|---|
| 3,736,321 | 5/1973 | Mee et al. | 544/345 |
| 4,492,702 | 1/1985 | Sherlock | 424/256 |
| 4,680,298 | 7/1987 | Blythin | 514/293 |
| 4,859,669 | 8/1989 | Duelfer et al. | 514/250 |

*Primary Examiner*—Mary C. Lee
*Assistant Examiner*—Joseph K. McKane
*Attorney, Agent, or Firm*—Gerald S. Rosen

[57] ABSTRACT

Tricyclic pyrrolo naphthyridinone compounds are disclosed, which are useful as antiinflammatory and anti-hyperprolferative agents.

18 Claims, No Drawings

ANTIINFLAMMATORY AND ANTI-HYPERPROLIFERATIVE COMPOUNDS

BACKGROUND OF THE INVENTION

The present invention relates to novel tricyclic compounds that possess antiinflammatory and anti-hyperproliferative activity. Other tricyclic and analogous antiinflammatory agents have been disclosed, i.e. U.S. Pat. No. 4, 680, 298 published PCT application 86/01269 and U.S. 4, 492, 702 (corresponding to European Patent application (0092786).

SUMMARY OF THE INVENTION

The invention relates to a compound having the structural formula I

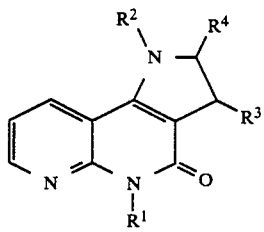

or pharmaceutically acceptable salts or solvates thereof wherein:

$R^1$ is selected from H, alkyl, aryl, alkenyl, benzyl, substituted alkyl, substituted aryl or substituted benzyl;

$R^2$ is selected from H, alkyl, aryl, alkenyl, benzyl, substituted alkyl, substituted aryl, substituted benzyl, —O(-CO)—$R^8$, —D—NR$^5$R$^6$, —D—OR$^7$ or —D—(-CO)—OR$^8$ wherein D is alkanediyl or a covalent bond;

$R^3$ and $R^4$ are the same or different and each is independently selected from H, alkyl, aryl or heteroaryl;

$R^5$ $R^6$ are the same or different and each is independently selected from H or alkyl, or together represent alkanediyl;

$R^7$ is selected from H, alkyl or aryl; and $R^8$ is selected from alkyl, aryl, benzyl or substituted benzyl.

A preferred subgenus of compounds is that wherein:

$R^1$ is selected from H, phenyl, benzyl, substituted phenyl or substituted benzyl;

$R^2$ is selected from H, phenyl, substituted phenyl, alkyl, allyl, —O(CO)—$R^8$, —D—NR$^5$R$^6$, —D—OH or —D—(CO)—OR$^8$ wherein D is alkanediyl or a bond;

$R^3$ and $R^4$ are the same or different and each is independently selected from H or alkyl;

$R^5$ and $R^6$ are the same or different and each is independently selected from H or alkyl, or together represent alkanediyl of from 1 to 8 carbon atoms; and $R^8$ is selected from alkyl or aryl.

A more preferred subgenus of compounds is that wherein:

$R^1$ is phenyl and $R^2$ is selected from H, phenyl, benzyl or carbethoxy; and $R^3$ and $R^4$ are H.

A still more preferred subgenus of compounds is that wherein:

$R^1$ is phenyl;

$R^2$ is selected from H, phenyl or carbethoxy; and $R^3$ and $R^4$ are H.

Preferred species are those having the names:

1,2,3,5-tetrahydro-1,5-diphenyl-4H-pyrrolo [3,2-c][1,8]naphthyridin-4-one;

1,2,3,5-tetrahydro-5-phenyl-I-(phenylmethyl)-4H-pyrrolo[3,2-c][1,8]naphthyridin-4-one;

2,3,4,5-tetrahydro-4-oxo-5-phenyl-1-H-pyrrolo[3,2-c[[1,8]naphthyridine-1-carboxylic acid, ethyl ester; or 1,2,3,5-tetrahydro-5-phenyl-4H-pyrrolo[3,2c][1,8]naphthyridin-4-one.

The invention also includes a pharmaceutical composition which comprises a compound having structural formula I in combination with a pharmaceutically acceptable carrier and a method for treating inflammation or hyperproliferative skin disease in a mammal that comprises administering an antiinflammatory or anti-hyperproliferative effective amount, respectively, of the above-defined compound to said mammal.

DESCRIPTION OF THE INVENTION

The starting materials having structural formulas II and III are known in the art. U.S. Pat. No. 4,492,702 and EP Patent 092786, which describe the preparation of compounds of formula II, are hereby incorporated by reference. Also, U.S. Pat. No. 4,680,298 which describes the preparation of compounds of formula III, is hereby incorporated by reference.

The compounds of formula I can be prepared by the processes A-G below, Wherein $R^1$, $R^2$, $R^3$, $R^4$, $R^5$, $R^6$, $R^7$ and D are as defined above unless otherwise indicated.

A. Compounds of formula I wherein $R^2$ is $R^{2a}$ and $R^{2a}$ is selected from alkyl, aryl, alkenyl, benzyl, substituted alkyl, substituted aryl, substituted benzyl, —D—NR$^5$R$^6$ or —DOR$^7$ (i.e., a compound of formula Ia below) can be produced by the following reaction:

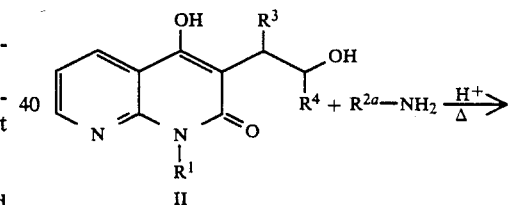

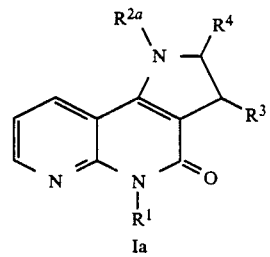

For example, Compound II may be treated With the amine ($R^{2a}$ NH$_2$) in the presence of a catalytic amount of acid and enough of a suitable solvent, for example lower-alkyl alcohol such as ethanol (EtOH), to dissolve the reagents. Preferably, the stoichiometry of Compound II:amine in the reaction is in the range of 1:1 to 1:10 and more preferably about 1:2. The acid can be any suitable strong acid including HCl or toluenesulfonic acid. Preferably the reaction is carried out under an inert atmosphere such as N$_2$ or Ar. The reaction may be performed at any effective temperature but is preferably heated to a temperature of at least about 100° C., preferably 100°-200° C. for an appropriate period, usually at least about 0.5 hours, preferably 0.5–3 hours. More preferably, the heating is at about 165° C. for about 1 hour. The reaction mixture may be triturated with aqueous base, preferably NaOH, and extracted with an organic solvent such as CH$_2$Cl$_2$ or ether. The organic layer is dried then evaporated. The residue can be purified by chromatography on silica and characterized and verified by TLC, spectral analysis, melting point and elemental analysis.

B. Compounds of formula I wherein R$^2$ is R$^{2a}$ as described above may be produced by the following reaction:

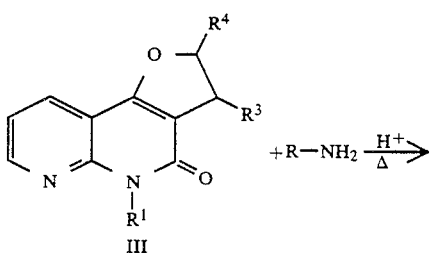

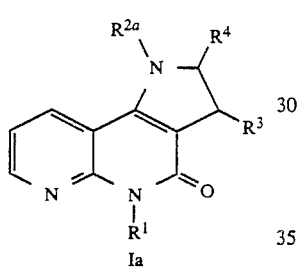

A compound of Type III, prepared as described in U.S. Pat. No. 4,680,298, is mixed with an amine R$^{2a}$-NH$_2$ (preferably an excess, more preferably 1 to 25 equivs.), which usually acts as the solvent. The mixture is preferably heated, more preferably to a temperature of between about 100° C. and 240° C., most preferably in the range of 150° to 210° C. Preferably, the reaction is also carried out in an inert atmosphere such as N$_2$. The reaction progress may be followed by TLC and/or HPLC until the starting material is consumed. When the reaction is sufficiently complete the product is cooled and extracted into an organic solvent, such as CH$_2$Cl$_2$ and is purified by flash chromatography on silica gel and characterized by spectral analysis, melting point and elemental analysis.

C. In addition, compounds of formula I wherein R$^2$ is R$^{2a}$ as defined above may be prepared by the following reaction:

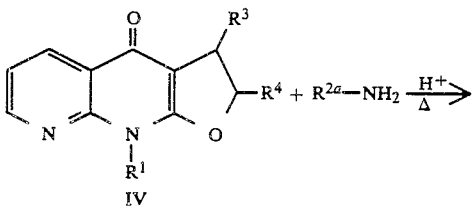

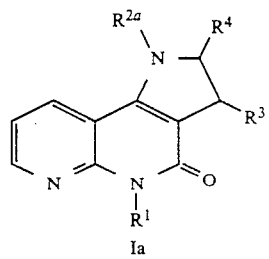

Compound IV may be obtained as described in U.S. Pat. No. 4,680,298 and the conditions for this reaction are essentially the same as those used in the process described above in Section B.

D. Compounds of formula I wherein R$^1$ and R$^2$ are the same and both are selected from the group described for R$^1$ above may be produced by the following reaction:

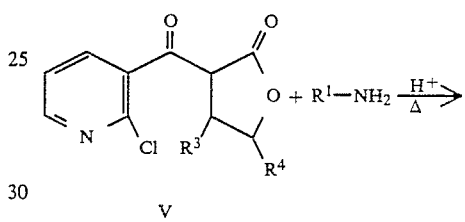

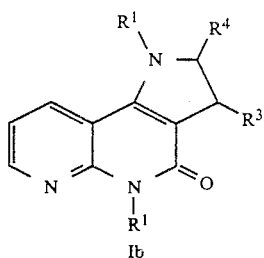

Compound V, whose synthesis is described in U.S. Pat. No. 4,680,298, is reacted with the amine R$^1$NH$_2$ using the conditions and stoichiometries described above in section A for the reaction of Compound II with R$^2$NH$_2$. Stoichiometries of at least 1:2 (Compound V: R$^1$ NH$_2$) are preferred. Characterization and verification of the product is as above.

E. Compounds of formula I wherein R$^2$ is H and R$^1$ is R$^{1a}$ wherein R$^{1a}$ is H, alkyl, aryl, alkenyl, substituted alkyl, substituted aryl or substituted alkenyl (Compound Id) can be produced by the following reaction:

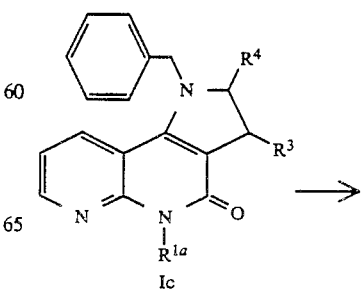

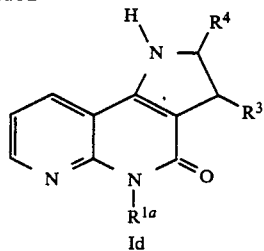

Compound Ic (wherein the benzyl group may also be substituted) may be mixed with a suitable strong acid, e.g. 30% HBr/acetic acid. Preferably the ratio of compound Ic to acid is from 1:1 to 1:10 w/w (Compound Ic:HBr solution). A ratio of 1:5 Compound Ic:HBr solution is more preferable. The reaction occurs at any effective temperature, preferably between 20°-120° C., preferably under an inert atmosphere (pressure about 1 atm) for at least 15 minutes, preferably 15 minutes to 4 hours. However, the reaction may be followed by TLC until sufficiently complete. Reaction at 90° C. under an $N_2$ or Ar atmosphere for about 1 hour is typical. The reaction mixture may be poured into water and neutralized to a pH of 4.0–8.0 (pH 5.0 is preferred). The product can be collected by filtration and characterized and verified as described above.

In addition, the benzyl (or substituted benzyl group) in the compound of formula Ic may be removed under standard hydrogenolysis conditions, e.g., by use of a suitable catalyst such as Pd on carbon under $H_2$ gas in a suitable solvent such as methanol, preferably in the presence of an acid such as acetic acid, HCl, trifluoroacetic acid, etc. The $H_2$ pressure is preferably in the range of from about 1 to about 4 atmospheres.

F. Compounds of formula I wherein $R^2$ is —D—C—(O)$OR^8$ (Compound Ie) can be produced by the following reaction:

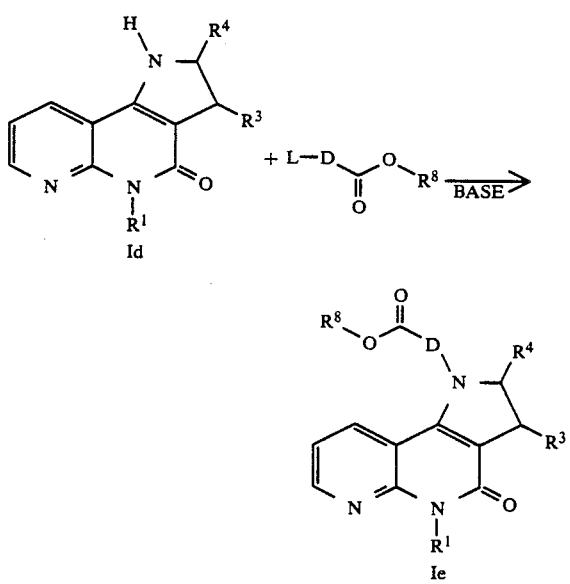

wherein L is a suitable leaving group such as chloro, bromo, tosyl, mesyl, etc.

Compound Id may be reacted in a suitable solvent such as $CH_2Cl_2$ with L—D—(CO)$OR^8$ Preferaby, a molar ratio of 1:1 to 1:10 (Compound Id: L—D—(-CO)$OR^8$) is employed. Suitable bases include triethyl- amine, pyridine, N, N-dimethylaminopyridine or $K_2CO_3$ Preferably, the reaction proceeds for at least 2 hours, preferably 2–48 hours. A ratio of 1:2 (Compound Id: solvent), the base N, N-dimethylaminopyridine and a reaction time of about 24 hours are typical. The product (Compound Ie) can be collected by filtration, washed with dilute acid such as 0.5N HCl, followed by washing with $H_2O$ and drying. The product can be characterized and verified as described above.

G. The compounds of formula Ig (i.e., compounds of formula I wherein $R^2$ is —O(CO)—$R^8$) may be prepared from compound If (compounds of formula I wherein $R^2$ is OH) by the following reaction:

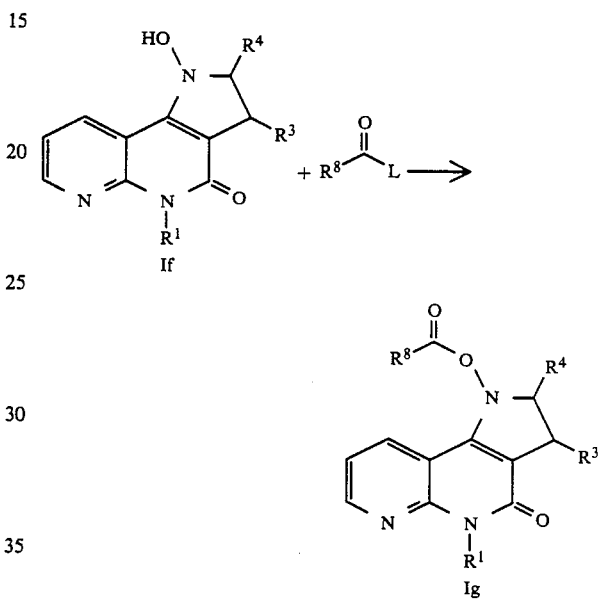

Compound If may be reacted with an acylating agent such as $R^8$(CO)L, wherein L is a suitable leaving agent such as Cl. The reaction may proceed under standard conditions for acylation reactions, in the presence of a suitable base, such as triethylamine ($NEt_3$). Standard conditions for acylation reactions are well known to those skilled in the art.

When utilized herein and in the appended claims, the following terms, unless specified otherwise, are defined as:

alkyl—straight and branched saturated carbon chains containing from 1 to 10 carbon atoms;

aryl—a carbocyclic group containing at least one benzene ring. Preferably the aryl groups contain from 6 to 15 carbon atoms, more preferably being phenyl or substituted phenyl, e.g., phenyl, naphthyl, indenyl, indanyl, 4-chlorophenyl, 4-fluorophenyl, etc.;

alkenyl—straight and branched carbon chains containing one or more carbon-carbon double bonds, attached to the nitrogen atom by a methylene (—$CH_2$—), e.g., an allyl group;

alkanediyl—divalent, saturated straight and branched carbon chains, preferably containing 1–8 carbon atoms;

heteroaryl—aryl groups having at least one O, S and/or N hetero atom interrupting the ring structure and having a sufficient number of unsaturated carbon to carbon bonds, nitrogen to carbon bonds, etc., to provide aromatic character, with the aromatic heterocyclic groups preferably containing from 2 to 14 carbon atoms, e.g., pyridyl, furyl, thienyl, thiazolyl, imidazolyl, pyrimidinyl, pyrazinyl, pyridazinyl, 1,2,4-triazinyl, benzofuranyl, indolyl, pyrazolyl, oxazolyl, etc. Many times such heterocyclic groups can be bonded via various carbon atoms on the heterocyclic ring and all such variations are contemplated, e.g. 2- or 3-furanyl, 2-, 3- or 4-pyridyl, 2-, 4- or 5-imidazolyl, etc.;

halogen—fluorine, chlorine, bromine and iodine;

alkoxy—an alkyl radical attached to a molecule by oxygen;

substituted alkyl—an alkyl wherein one or more hydrogens is replaced by OH;

substituted aryl, substituted benzyl, or substituted phenyl—an aryl, benzyl or phenyl wherein one or more aromatic hydrogen is replaced by the same or different substituents independently chosen from hydroxy, alkyl having from 1 to 6 carbon atoms, halogen, nitro, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, $S(O)_p R^a$ [wherein p is 0, 1 or 2 and $R^a$ is alkyl having from 1 to 6 carbon atoms].

Certain compounds of this invention may exist in isomeric forms. The invention contemplates all such isomers both in pure form and in admixture, including racemic mixtures.

Certain compounds of the invention of formula I can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

Certain compounds of the invention will be acidic in nature, e.g. those compounds which possess a carboxyl or phenolic hydroxyl group. These compounds may form pharmaceutically acceptable salts. Examples of such salts are the sodium, potassium, calcium, aluminum, gold and silver salts. Also contemplated are salts formed with pharmaceutically acceptable amines such as ammonia, alkylamines, hydroxyalkylamines, N-methylglucamine and the like.

The antiinflammatory activity of the compounds can be demonstrated by standard test procedures, such as the reversed passive arthus reaction (RPAR) as described below or as described in Myers et al., Inflammation 9(1):91–98 (1985).

The antiinflammatory activity and antiproliferative activity of the compounds can be demonstrated by using the lipoxygenase assay described below.

Reversed Passive Arthus Reaction (RPAR) Animals, Materials and Methods

Male Lewis inbred albino rats weighing 180–220 grams obtained from Charles River Breeding Laboratories are used in these experiments. The rats are housed 3 animals/cage and food and water are allowed ad libitum.

The animals are numbered 1–3 in each cage and color marked for identification purposes.

All reagents and drugs are prepared just prior to the study. Crystallized and lyophilized bovine serum albumin (BSA), obtained from Sigma Chemical Company, is solubilized without shaking in cold sterile pyrogen free saline (10 mg/ml). Lyophilized anti-bovine serum albumin (IgG Fraction), obtained from Cappel Laboratories, is suspended in sterile distilled water and diluted with cold pyrogen free saline (PFS) just prior to use. The final concentration of anti-bovine serum albumin is 0.5 mg/ml of PFS. Both BSA and anti-BSA solutions are iced during use. Drugs are suspended or solubilized in an aqueous solution of methyl cellulose (MC) with a homogenizer just prior to administration.

Groups of animals (6/group) are dosed with drug in MC by gavage one hour prior to sensitization with BSA. Controls are given MC alone and drug-standard is usually included in each assay for verification purposes. Drugs are prepared so as to provide a dose for a 200 gram animal which is equivalent to the mg/kg dose for the experiment. Thus each rat receives an oral dose in a volume of approximately 2.0 cc. One hour after dosing the animals are lightly anesthetized with ether and sensitized by injecting into the penile vein 0.2 ml of PFS containing 1.0 mg of BSA. One hour later they are injected in the plantar region of one hind paw with 0.1 ml of PFS containing 1.0 mg of BSA. One hour later they are injected in the plantar region of one hind paw with 0.1 ml of PFS containing 0.1 mg of the anti-bovine serum albumin. Immediately after the subplantar injection, the injected paw is dipped (up to the lateral maleolus) into the mercury well of a plethysmograph. The volume of mercury displaced is converted to weight and recorded. This value is considered to be the control paw volume for the animal. Paw volumes are also recorded with a plethysmograph during the development of the inflammation at 2 and 4 hours post-challenge. Compound 1,2,3,5 tetrahydro-5-phenyl-4H-pyrrolo[3,2c][,1]naphthyridin-4-one provided an $ED_{50}$ value of about 25 mg/kg, p.o. in this procedure.

Another procedure for testing for acute antiinflammatory activity measures the reverse passive Arthus reaction in the pleural cavity of rats as described in Myers et al., Inflammation, Vol. 9, No. 1, 1985, pp. 91–98. Compounds 1,2,3,5 tetrahydro-5-phenyl-4H-pyrrolo[3,2-c][,1]naphthyridin-4-one and 2,3,4,5- tetrahydro-4-oxo-5-phenyl-1H-pyrrolo[3, 2-c][b 1,8]-naphthyridin-1-carboxylic acid, ethyl ester provided $ED_{50}$ values of less than 25 mg/kg and about 25 mg/kg respectively, p.o. in this procedure.

The effect of the compounds of the invention on 5-lipoxygenase activity is determined using rat neutrophils. Male Wistar-Lewis rats are injected intravenously with 5 mg BSA in 0.2 ml pyrogen free saline followed by an intrapleural injection of 500 ug of the IgG fraction of rabbit anti-BSA (Cappel Labs., Lot 17782) in 0.2 ml pyrogen free saline. Injections are made under light ether anesthesia. Four hours later, the pleural cavity exudate consisting of 85 to 95% neutrophils is removed. Neutrophils are isolated from the pleural exudates by centrifugation of 4° C. for 10 min at 200×g. The cell pellet is resuspended in 17 mM Tris HCl buffer, pH 7.2, containing 0.75% $NH_4Cl$ to lyse contaminating erythrocytes followed by centrifugation at 4° C. for 5 min at 200×g. The pelleted neutrophils are rewashed in 50 mM Tris HCl, pH 7.4, containing 100 mM NaCl, followed by the same centrifugation. The cell pellet is resuspended in 50 mM Tris HCl, pH 7.4, containing 100 mM NaCl and 1 mM $CaCl_2$, at $3-12 \times 10^7$ intact neutrophils per ml.

Solutions of compounds in methanol are dried, then resuspended in the cell suspension for 4 min. Arachidonic acid metabolism is determined by incubating 0.1 ml of this suspension with 40 uM [$\times ^{14}C$] arachidonic acid (AA) (Amersham, 59 Ci/mole), in the presence of 0.1% BRIJ 56 and 10 uM A23187. Arachidonic acid metabolism as well as the various drug and reagent abbreviations are described in detail in Arch. Dermatol, Vol. 119, pages 541 to 547 (July 1983), the teachings of which are incorporated herein by reference. Assays run in triplicate are initiated by adding cells with inhibitor to a film of the BRIJ 56, arachidonic acid and A23187 at 37° C. After one minute, reactions are terminated by the addition of 2.4 ml of a chloroform:methanol (1:1 v/v) mixture and 0.9 ml of 0.1% formic acid. The suspension is vortexed, immediately cooled on ice, centrifuged, and the organic layer withdrawn. The extract is evaporated under a stream of $N_2$ and resuspended in 0.1 ml chloroform:methanol (2:1 v/v) for spotting on thin layer plates (Sil G-25, without gypsum, Brinkmann). Chromatograms are developed with ether:methanol (80:20) for 2 cm, dried, and redeveloped with ligroine: diethylether:-glacial acetic acid (40:60:1 v/v/v) for an additional 20 cm. Products, leukotriene $B_4$ ($LTB_4$), 12-hydroxy heptadecatrienoic acid (HHT) and 5-hydroxy icosatetraenoic acid (5-HETE), are located by autoradiography and appropriate regions of the thin layer plates are scraped and counted in a liquid scintillation counter. Metabolites are identified by co-chromatography with authentic standards.

Compound , 1,2,3,5-tetrahydro-1,5-diphenyl-4-H-pyrrolo[3,2-c][1,8]naphthyridin-4-one showed about 40% inhibition of HHT production and 60% inhibition of HETE and $LTB_4$ production when the compound was present in a concentration of $5 \times 10^{-5}$ Molar.

The compounds in this invention can thus be used to treat inflammation and hyperproliferative skin diseases.

As used herein, the term "hyperproliferative skin disease" means any condition a symptom of which is accelerated skin cell production, flaking, scales or papular lesions, including, for example psoriasis, eczema, dandruff and the like.

In the preferred antiinflammation use, the compounds of this invention are used to treat patients by administering an anti-inflammatory effective amount thereof.

The active compounds can be administered orally, topically, parenterally, or by oral or nasal inhalation. The preferred mode of administration is orally or intravenously.

Formulations for topical application, e.g., for use in treating hyperproliferative skin diseases, may include the above liquid forms, creams, aerosols, sprays, dusts, powders, lotions and ointments which are prepared by combining an active ingredient according to this invention with conventional pharmaceutical diluents and carriers commonly used in topical dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oily base and will, in general, also include one or more of the following, namely, stabilizing agents, emulsifying agents, dispersing agents, suspending agents, thickening agents, coloring agents, perfumes and the like.

Powders may be formed with the aid of any suitable powder base, e.g., talc, lactose, starch, etc. Drops may be formulated with an aqueous base or non-aqueous base also comprising one or more dispersing agents, suspending agents, solubilizing agents, etc.

The topical pharmaceutical compositions according to the invention may also include one or more preservatives or bacteriostatic agents, e.g., methyl hydroxybenzoate, propyl hydroxybenzoate, chlorocresol, benzalkonium chlorides, etc.

The topical pharmaceutical compositions according to the invention may also contain other active ingredients such as antimicrobial agents, particularly antibiotics, anesthetics, analgesics and antipruritic agents.

The amount and frequency of administration will be regulated according to the judgement of the attending clinician considering such factors as age, condition and size of the patient as well as severity of the disease being treated. A typical recommended dosage regimen for treating inflammation is oral administration of from 0.5 to 50 mg/kg/day preferably 2 to 40 mg/kg/day, in two to four divided doses to achieve relief of the symptoms. Alternatively, intravenous administration of 0.1 to 10 mg/kg/day is recommended, preferably 0.6 to 8 mg/kg/day in two to four divided doses to achieve relief of the inflammation symptoms. When administered orally or parenterally for the treatment of hyperproliferative skin disease, the compounds may be administered in an amount ranging from about 0.01 mg/kg to about 100 mg/kg, and preferably from about 0.1 mg/kg to about 10 mg/kg. When administered topically, the compounds of the invention can be administered in any pharmaceutically acceptable dosage form, such as a cream, ointment, lotion, solution, transdermal patch, etc., in an amount ranging from about 0.001 mg to about 100 mg per dose, preferably from about 0.01 to about 10 mg per dose.

The compounds can be administered in conventional oral dosage forms such as capsules, tablets, pills, powders, suspensions or solutions prepared with conventional pharmaceutically acceptable excipients and additives, using conventional techniques. Parenteral preparations, i.e. sterile solutions or suspensions are also made by conventional means. Inhalation administration can be in the form of a nasal or oral spray. Insufflation is also contemplated. Topical dosage forms can be creams, ointments, lotions and the like. Other dosage forms which can be used are transdermal devices.

The following examples illustrate the preparation of the compounds used in the methods of this invention as well as pharmaceutical compositions containing the compounds. All temperatures are in degrees Celsius.

EXAMPLE I

Preparation of 1,2,3,5-tetrahydro-1,
5-diphenyl-4H-pyrrolo[3,2-c][1,8]napthyridin-4-one A. The following reagents were combined in a 5 mL vessel: 2(2-chloronicotinoyl)butyrolactone (II) 0.500 g (2.22 mmol), aniline 0.500 mL (4.44 mmol), and 2.0 mL MeOH (Me=$CH_3$). The vessel was purged with argon and kept under argon during the course of the reaction. The reaction mixture was heated to about 165° C. over a period of 2hr, held at about 165° C. for an additional κ hr and then allowed to cool to room temperature. The reaction mixture was triturated with 10 mL of 10% NaOH and 10 mL $CH_2Cl_2$. The $CH_2Cl_2$ layer was collected and evaporated to give 0.810 g of crude product.

The crude product was purified by preparative TLC using 90:10 n-BuCl:MeOH (Bu=$C_4H_9$) on silica. Yield after extraction and drying was 0.210 g (0.605 mmol, 27.2%), mp 220-2° C. IR, NMR, and MS spectra were consistent with the assigned structure. C, H, and N analyses were within 0.3% of theory.

This procedure will also produce 1,2,3,5-tetrahydro-1,5-bis(3-chlorophenyl)-4H-pyrrolo [3,2-c][1,8]naphthyridin-4-one when 3-chloroaniline is substituted for aniline.

B. A mixture of 1-phenyl-3-(2-hydroxyethyl)-4-hydroxy-[1,8]naphthyridin-2-one (III) 0.500g (1.73 mmol), aniline 0.500 mL (4.44 mmol), 2.00 mL EtOH, (Et=$C_2H_5$) and 50 ul 6 N HCl was charged into a 5 mL vessel under argon and heated to about 165° C. over a period of 2hr, then held at about 165° C. for an additional ½ hr and then allowed to cool to room temperature. The reaction mixture was triturated with 10 mL of 10% NaOH and 10 mL $CH_2Cl_2$. The $CH_2Cl_2$ layer was collected and evaporated to give 0.712 g of crude product.

The crude product was purified by preparative TLC using 90:10 n-BuCl:MeOH (Bu=$C_4H_9$) on silica. Yield after extraction and drying was 0.331 g (0.976 mmol, 56.4%), mp 220°-222° C. IR, NMR, and MS were consistent with the assigned structure.

This procedure will also produce 1,2,3,5-tetrahydro-1-(4-methoxyphenyl)-5-phenyl-4-H-pyrrolo [3,2-c][1,8]naphthyridin-4-one when 4-methoxyaniline (also known as p-anisidine) is substituted for aniline

EXAMPLE II

Preparation of 1,2,3,5-tetrahydro-5-phenyl-1-(phenylmethyl)-4H-pyrrolo[3,2-c][1,8] napthyridin-4-one A. A mixture of 0.500 g 1-phenyl-3-(2-hydroxyethyl)-4-hydroxy-[1,8]naphthyridin-2-one (III) (1.73 mmol), 0.500 g benzylamine hydrochloride (3.44 mmol), and 2.00 mL EtOH was charged into a 5 mL vessel under argon and heated to about 200° C. over a period of about 2hr, held at about 200° C. for an additional 1h and then allowed to cool to room temperature. The reaction mixture was triturated with 5×10 mL $H_2O$ then with 5×10 mL of 10% NaOH. The resulting amorphous solid was washed with $H_2O$ and extracted with 2×15 mL refluxing toluene. Evaporation of the toluene produced crude product. Purification by preparative TLC (n-BuCl:MeOH::85:15 on silica) yielded 0.123 g (0.385 mmol, 9.8%) crystalline solid. IR, NMR, and MS spectra were consistent with the assigned structure.

This procedure will also produce 1,2,3,5-tetrahydro-5-(3-chlorophenyl)-2-methyl-I-(phenylmethyl)-4H-pyrrolo[3,2-c][1,8]naphthyridin-4-one when 1-(3-chlorophenyl)-3-(2-hydroxypropyl)-4-hydroxy-[1,8]naphthyridin-2-one is substituted for 1-phenyl-3-(2-hydroxyethyl)-hydroxyethyl)-4-hydroxy-[1, 8]naphthyridin-2-one. Furthermore, 1,2,3,5-tetrahydro-5-(3-methoxyphenyl)-1-hydroxy-2-methyl-4H-pyrrolo[3,2-c][1,8]naphthyridin-4-one is produced by this procedure when 4-hydroxy-1-(3-methoxyphenyl)-3-(2-hydroxypropyl)-[1,8]naphthyridin-2-one is substituted for 1-phenyl-3-(2-hydroxyethyl)-4-hydroxy-[1,8]naphthyridin-2-one and hydroxylamine hydrochloride is substituted for benzylamine hydrochloride.

B. A suspension of 3,5-dihydro-5-phenylfuro[3,2-c][1,8]naphthyridin-4 (2H)-one (2 g), (formula III) in benzylamine (6 mL) was heated in an inert atmosphere ($N_2$) at 160-165° C. until the starting material (formula III) had disappeared (about 24 hours), as shown by HPLC (Reverse phase $C_{18}$ column; solvent; $CH_3CN$ (65); $H_2O$(35); $CH_3CO_2H$ (0.5)). The reaction time was about 24 hr. After cooling, the crude product was treated with ether and the solid which formed was filtered off, washed with ether and triturated with isopropanol. The yield of product was 0.75 g, identical with the material from Example IIA.

This procedure will also produce 1,2,3,5-tetrahydro-I-(n-butyl)-5-phenyl-4H-pyrrolo[3,2-c] [1,8]naphthyridin-4-one when 1-phenyl-3-(2-hydroxyethyl)-4-hydroxy-[1,8]naphthyridin-2-one is substituted for 3,5-dihydro-5-phenyl-furo[3,2-c][1,8]naphthyridin-4(2H)-one and n-butylamine is substituted for benzylamine. Furthermore, 1,2,3,5-tetrahydro-5-(3-chlorophenyl)-1-(2-hydroxyethyl)-2-methyl-4H-pyrrolo[3,2-c][1,8] naphthyridin-4-one may be produced by this procedure when 1-(3-chlorophenyl)-4-hydroxy-3-(2-hydroxypropyl)[1,8]naphthyridin-2-one is substituted for 3,5-dihydro-5-phenyl-furo[3,2-c][1,8]naphthyridin-4(2H)-one and 2-hydroxyethylamine is substituted for benzylamine.

EXAMPLE III

Preparation of 1,2,3,5-tetrahydro-5-phenyl-4H-pyrrolo[3,2-c][I, 8]napthyridin-4-one Compound I (5.0 g) where $R^1$=phenyl, $R^2$=benzyl, $R^3$=$R^4$=H and X was CH was mixed with 30% HBr in HOAc (25 mL). The reaction was heated to about 90° C. under an $N_2$ atmosphere for about 1 hr. The reaction mixture was then poured into water (300mL). The resulting mixture was adjusted to a pH of 5.0 with NaOH solution. The product was collected by filtration. Yield was 43%, mp was >290° C. gmax in MeOH were 324 nm (e=10500) and 354 nm (e=5500).

This procedure will also produce 1,2,3,5-tetrahydro-5-(3-chlorophenyl)-4H-pyrrolo[3,2c][1,8]naphthyridin-4-one when 1,2,3,5-tetrahydro-5-(3-chlorophenyl)-1-(phenylmethyl)-4H-pyrrolo[3,2-c] [1,8]naphthyridin-4-one is substituted for the starting material compound I where $R^1$ is phenyl, $R^2$ is benzyl and $R^3$ and $R^4$ are H. Furthermore, 1,2,3,5-tetrahydro-5-(4-fluorophenyl)-2-methyl-4H-pyrrolo[3,2-[1,8]naphthyridin-4-one may be produced by this procedure when 1,2,3,5-tetrahydro-5-(4-fluorophenyl)-2-methyl-1-(phenylmethyl)-4H-pyrrolo[3,2-c][1,8]naphthyridin-4-one is substituted for the starting material compound I as defined above.

EXAMPLE IV

Preparation of 2,3,4,5-tetrahydro-4-oxo-5-phenyl-1H-pyrrolo[3,2-c][1,8]napthyridine-1-carboxylic acid, ethyl ester Compound I (300 mg) where $R^1$=phenyl and $R^2$=$R^3$=$R^4$=H was reacted in $CH_2Cl_2$ (6 mL) with ClC(O)OEt (0.7 mL) in the presence of excess N, N-dimethylaminopyridine for 24 hr. The product was collected by filtration, washed with dilute acid (0.5 N HCl) then with $H_2O$ and dried. Yield was 83%, m.p. is 230-233° C.

This procedure will also produce 2,3 4,5-tetrahydro-4-oxo-5-(3-chlorophenyl)-1H-pyrrolo[3,2c] 1,8]naphthyridine-1-carboxylic acid, 2-methylpropylester when 1,2,3,5-tetrahydro-5-(3-chlorophenyl)-4H)-pyrrolo[3,2-c] naphthyridin-4-one is substituted for the starting material compound I where $R^1$ is phenyl and $R^2$, $R^3$ and $R^4$ are H.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:
1. A compound having the structural formula I

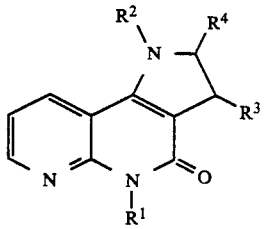

or a pharmaceutically acceptable salt or solvate thereof, wherein:

$R^1$ is selected from H, alkyl having from 1 to 10 carbon atoms, aryl having from 6 to 15 carbon atoms, alkenyl having from 3 to 10 carbon atoms, benzyl, substituted alkyl having from 1 to 10 carbon atoms substituted aryl having from 6 to 15 carbon atoms, or substituted benzyl;

$R^2$ is selected from H, alkyl having from 1 to 10 carbon atoms, aryl having from 6 to 15 carbon atoms, alkenyl having from 3 to 10 carbon atoms, benzyl, substituted alkyl having from 1 to 10 carbon atoms, substituted aryl having from 6 to 15 carbon atoms, substituted benzyl, —O(CO)—$R^8$, —D—$NR^5R^6$, —D—$OR^7$ or —D—(CO)—$OR^8$ wherein D is alkanediyl having from 1 to 8 carbon atoms or a covalent bond; '$R^3$ and $R^4$ are the same or different and each is independently selected from H, alkyl having from 1 to 10 atoms, aryl having from 6 to 15 carbon atoms or heteroaryl selected from the group consisting of pyridyl, furyl, thienyl, thiazolyl, imidazolyl, pyrimidinyl, pyrazinyl, pyridazinyl, 1,2,4-triazinyl, benzofuranyl, indolyl, pyrazolyl, and oxazolyl having from 2 to 14 carbon atoms;

$R^5$ and $R^6$ are the same or different and each is independently selected from H or alkyl having from 1 to 10 carbon atoms or together represent alkanediyl having from 1 to 8 carbon atoms;

$R^7$ is selected from H, alkyl having from 1 to 10 carbon atoms or aryl having from 6 to 15 carbon atoms; and $R^8$ is selected from alkyl having from 1 to 10 carbon atoms, aryl having from 6 to 15 carbon atoms benzyl or substituted benzyl.

2. The compounds of claim 1 wherein:
$R^1$ is selected from phenyl, benzyl, substituted phenyl or substituted benzyl;
$R^2$ is selected from H, phenyl, substituted phenyl, alkyl having from 1 to 10 carbon atoms, alkenyl having from 3 to 10 carbon atoms, —O(CO)—$R^8$, —D—$NR^5R^6$, —D—OH or —D—(CO)—$OR^8$ wherein D is alkanediyl having from 1 to 8 carbon atoms or a covalent bond;
$R^3$ and $R^4$ are the same or different and each is independently selected from H or alkyl having from 1 to 10 carbon atoms;
$R^5$ and $R^6$ are the same or different and each is independently selected from H or alkyl having from 1 to 10 carbon atoms, or together represent alkanediyl having from 1 to 8 carbon atoms; and
$R^8$ is selected from alkyl having from 1 to 10 carbon atoms or aryl having from 6 to 15 carbon atoms.

3. The compounds of claim 2 wherein said substituent on said substituted phenyl or substituted benzyl is selected from halogen, nitro, alkyl having from 1 to 10 carbon atoms or alkoxy having from 1 to 10 carbon atoms.

4. The compounds of claim 2 wherein $R^1$ is phenyl; and
$R^2$ is selected from phenyl, benzyl, H or —(CO)$OR^8$.

5. The compounds of claim 4 wherein $R^2$ is H or —(CO)$OR^8$.

6. The compounds of claim 5 wherein $R^2$ is H.

7. The compounds of claim 5 wherein $R^2$ is —(CO)$OR^8$.

8. The compounds of claim 4 wherein $R^2$ is benzyl.

9. The compounds of claim 4 wherein $R^2$ is phenyl.

10. The compounds of claim 4 wherein $R^3$ and $R^4$ are H.

11. A compound of claim 1 having the name:
1,2,3,5-tetrahydro-1,5-diphenyl-4H-pyrrolo [3,2-c][1,8]naphthyridin-4-one;
1,2,3,5-tetrahydro-5-phenyl-1-(phenylmethyl)-4H-pyrrolo[3,2-c][1,8]naphthyridin-4-one;
2,3,4,5-tetrahydro-4-oxo-5-phenyl-1H-pyrrolo[3,2-c[[1,8]naphthyridine-1-carboxylic acid, ethyl ester;
1,2,3,5-tetrahydro-5-phenyl-4H-pyrrolo[3,2c][1,8-]naphthyridin-4-one;
1,2,3,5,-tetrahydro-1,5-bis(3-chlorophenyl)-4H-pyrrolo[3,2-c][1,8]naphthyridin-4-one;
1,2,3,5-tetrahydro-(4-methoxyphenyl)-5-phenyl-4H-pyrrolo[3,2-c][1,8]naphthyridin-4-one;
1,2,3,5-tetrahydro-5-(3-chlorophenyl)-2-methyl-1-(phenylmethyl)-4H-pyrrolo[3,2-c][1,8]naphthyridin-4-one;
1,2,3,5-tetrahydro-5-(3-methoxyphenyl)-1-2-methyl-4H-pyrrolo[3,2-c][l, 8]naphthyridin-4-one;
1,2,3,5-tetrahydro-1-(n-butyl)-5-phenyl-4H-pyrrolo[3,2-c][1, 8]naphthyridin-4-one;
2,3,5-tetrahydro-5-(3-chlorophenyl)-1-(2-hydroxyethyl)-2-methyl-4H-pyrrolo[3,2-c] [1,8]naphthyridin-4-one;
1,2,3,5-tetrahydro-5-(3-chlorophenyl)-4H-pyrrolo[3,2-c] [1,8]naphthyridin-4-one;
1,2,3,5-tetrahydro-5-(4-fluorophenyl)-2-methyl- 4H-pyrrolo [3,2-c] [1,8]naphthyridin-4-one; and
2,3,4,5-tetrahydro-4-oxo-5-(3-chlorophenyl)-1H-pyrrolo [3,2-c][1,8]naphthyridine-1-carboxylic acid, 2-methylpropylester.

12. A pharmaceutical composition which comprises an effective amount of a compound having structural formula I as defined in claim 1, in combination with a pharmaceutically acceptable carrier.

13. A method for treating inflammation in a mammal comprising administering to said mammal an antiinflammatory effective amount of a compound as claimed in claim 1.

14. The method of claim 13 wherein said antiinflammatory effective amount is 0.5 to 50 mg/kg/day, administered orally.

15. The method of claim 13 wherein said antiinflammatory effective amount is 0.1 to 10 mg/kg/day, administered intravenously.

16. A method for treating hyperproliferative skin disease in a mammal comprising administering to said mammal an anti-hyperproliferative effective amount of a compound as claimed in claim 1.

17. The method of claim 16 wherein said anti-hyperproliferative effective amount is 0.01 to 100 mg/kg, administered orally or parenterally.

18. The method of claim 16 wherein said anti-hyperproliferative effective amount is 0.001 to 100 mg/kg administered topically.

* * * * *